United States Patent [19]

Jacquet et al.

[11] 4,390,689
[45] Jun. 28, 1983

[54] POLYCATIONIC POLYMERS AND THEIR PREPARATION

[75] Inventors: Bernard Jacquet, Antony; Gérard Lang, Epinay sur Seine; Alain Malaval, Aulnay sous Bois; Serge Forestier, Claye Souilly; Do Le Trung, Drancy, all of France

[73] Assignee: Societe Anonyme dite: L'Oreal, Paris, France

[21] Appl. No.: 217,403

[22] Filed: Dec. 17, 1980

[30] Foreign Application Priority Data

Dec. 21, 1979 [FR] France .................................. 79 31432

[51] Int. Cl.³ .............................................. C08G 69/26
[52] U.S. Cl. ..................................... 528/335; 528/220; 528/229; 528/336; 528/363; 528/367; 528/392; 528/397; 528/422; 528/423; 424/70
[58] Field of Search ............... 528/335, 367, 336, 229, 528/220, 397, 422, 423, 392, 363

[56] References Cited

U.S. PATENT DOCUMENTS

| | | | |
|---|---|---|---|
| 3,671,468 | 6/1972 | Tsuda et al. | 528/392 |
| 3,856,714 | 12/1974 | Moore et al. | 528/423 |
| 4,075,136 | 2/1978 | Schaper | 528/397 |
| 4,157,388 | 6/1979 | Christiansen | 528/367 |
| 4,166,894 | 9/1979 | Schaper | 528/310 |
| 4,254,255 | 3/1981 | Lobach et al. | 528/310 |

*Primary Examiner*—Harold D. Anderson
*Attorney, Agent, or Firm*—Cushman, Darby & Cushman

[57] ABSTRACT

Polycationic polymers have been prepared and have been found to be useful in cosmetic compositions for the treatment of the hair and skin, or in the treatment of natural and synthetic textile fibers. These polymer comprise units of the formula

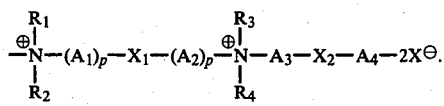

27 Claims, No Drawings

POLYCATIONIC POLYMERS AND THEIR PREPARATION

The present invention relates to new cationic type polymers, to their preparation and to their use.

More specifically, the present invention relates to polymers having units of the formula:

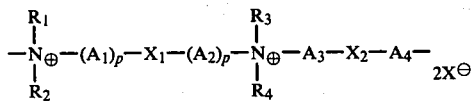

wherein $R_1$, $R_2$, $R_3$ and $R_4$, each independently represent a hydrocarbon group, optionally substituted, containing up to 20 carbon atoms,
or the pairs, $R_1$ and $R_2$, and/or $R_3$ and $R_4$, together, with the nitrogen atom to which they are attached, form a hetero-cycle which can contain one or more other oxygen or sulfur heteroatoms;
$A_1$, $A_2$, $A_3$ and $A_4$, each independently represent an alkylene or arylene group, substituted or not, containing up to 20 carbon atoms of carbon;
p is equal to 0 or 1;
when p=0, $X_1$ represents $-C_6H_4-CO-C_6H_4-$, $-C_6H_4-CHOH-C_6H_4-$,

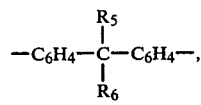

or $-C_6H_{10}-(CH_2)_n-C_6H_{10}-$
wherein n is a whole number ranging from 1 to 6, and $R_5$ and $R_6$ each independently represent hydrogen or alkyl, substituted or not, containing up to 20 carbon atoms, or $R_5$ and $R_6$, together, with the carbon atom to which they are attached, form a ring with 5 or 6 chains; and
when p=1, $X_1$ represents:
$-N(R_7)-(CO-X_3)_y-CO-N(R_8)-$,
$-CO-O-$, $-CO-NH-$, $-O-CO-NH-$,
$-CO-X_4-CO-$,
$-O-CO-X_5-CO-O-$, $-O-$, $-S-$, $-SO-$, $-SO_2-$,
$-S-S-$ or $-N(R_9)-$,
wherein $X_3$ represents alkylene, optionally interrupted by an $-S-S-$ group, alkenylene, arylene, diaminoalkylene, diaminoarylene, dioxyalkylene, polyoxyalkylene or dioxyarylene,
or $X_3$ represents a direct covalent bond,
$X_4$ represents diaminoalkylene, dioxyalkylene, diaminoarylene, dioxyarylene, polyoxyalkylene or dithioalkylene,
$X_5$ represents alkylene or arylene, substituted or not, or diaminoalkylene, diaminocycloalkylene or diaminoarylene, optionally substituted,
y is equal to 0 or 1,
$R_7$, $R_8$ and $R_9$ each independently represent hydrogen or alkyl containing up to 12 carbon atoms;
$X_2$ represents:
$-N(R_{10})-(CO-X_3)_z-CO-N(R_{11})-$,
$-CO-O-$, $-CO-NH-$, $-O-CO-NH-$,
$-CO-X_4-CO-$ or $-O-CO-X_5-CO-O-$,
wherein $X_3$, $X_4$ and $X_5$ have the meaning given above, z is 0 or 1, and $R_{10}$ and $R_{11}$ each independently represent hydrogen or alkyl containing up to 12 carbon atoms;
with the proviso that when p=1 and $X_1$ represents a heteroatom, z is other than 0.

In the following description those polymers based on recurring units of Formula I, above, are designated by the expression, "Formula I polymers."

The terminal groups of Formula I polymers can vary, particularly with regard to the proportions of the reagents used in preparing them. For example, they can be of the

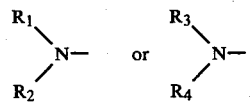

type, or of the $XA_1$-, $XA_2$-, $XA_3$- or $XA_4$-type.

In Formula I, the substituents $R_1$, $R_2$, $R_3$ and $R_4$ represent, in particular, alkyl, cycloalkyl, alkenyl, aryl or aralkyl, substituted or not. For example, $R_1$, $R_2$, $R_3$ and $R_4$ can represent alkyl or hydroxyalkyl, having from 1 to 8 carbon atoms, cycloalkylalkyl having less than 20 carbon atoms and preferably having not more than 16 carbon atoms, cycloalkyl having 5 or 6 chains, aralkyl such as a phenylalkyl wherein the alkyl moiety has, preferably, 1 to 3 carbon atoms. In particular, $R_1$, $R_2$, $R_3$ and $R_4$ are alkyl having from 1 to 10 carbon atoms. When $R_1$ and $R_2$, or $R_3$ and $R_4$ are attached to their respective nitrogen atoms so as to form a ring, the ring can have 5 or 6 chains, and can also include one or more other heteroatoms, particularly oxygen or sulfur. $A_1$, $A_2$, $A_3$ and $A_4$ represent, in particular, linear or branched alkylene having from 1 to 12 carbon atoms in the chain, and can optionally include one or more (particularly, 1 to 4) branched alkyl substituents, said branched substituents having, in particular, from 1 to 10, and especially from 1 to 4, carbon atoms. $X_1$, in particular, represents
$-NHCONH-$, $-S-S-$,
$-O-CO-NH-$alkylene$-NH-CO-O-$,
$-CO-NH-$alkylene$-NH-CO-$,
$-NHCOCONH-$, $-NH-CO-C_6H_4-CO-NH-$,
$-O-CO-$alkylene$-CO-CO-$,
$-CO-NH-$, $-CO-O-$, or $-CO-O-$alkylene$-O-CO-$;
In particular, $X_2$ represents
$-CO-NH-$alkylene$-NH-CO-$,
$-NH-CO-$alkylene$-CO-NH-$,
$-NH-CO-C_6H_4-C_6H_4-CO-NH-$,
$-O-CO-C_6H_4-CO-O-$,
$-O-CO-$alkylene$-CO-O-$,
$-CO-O-$, $-CO-NH-$ or $-CO-O-$(polyalkoxy)$-CO-$,
wherein the alkylene moiety is defined as above in the definition of $A_1$, $A_2$, $A_3$ and $A_4$,
$X^\oplus$ represents an anion derived from a mineral acid or from a low molecular weight organic acid, and, is in particular, a halide, sulfate, acetate or paratoluene sulfonate anion.

It should be noted the invention encompasses polymers of Formula I wherein the

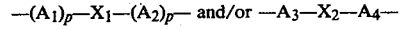

moieties have several different values in a single polymer chain.

The invention is not limited to Formula I polymers having a particular molecular weight range.

In general, the polymers of the present invention have an average molecular weight ranging between approximately 1,000 and 50,000.

The present invention also relates to a process for preparing the Formula I polymers.

This process consists in polycondensing at least one amine having the formula:

$$\begin{array}{cc} R_1 & R_3 \\ | & | \\ N-(A_1)_p-X_1-(A_2)_p-N \\ | & | \\ R_2 & R_4 \end{array} \quad (II)$$

or $$\begin{array}{cc} R_1 & R_3 \\ | & | \\ N-A_3-X_2-A_4-N \\ | & | \\ R_2 & R_4 \end{array} \quad (III)$$

with one or more dihalides having the formula:

$$X-A_3-X_2-A_4-X \text{ or } X-(A_1)_p-X_1-(A_2)_p-X.$$

The polycondensation reaction is carried out in a solvent or mixture of solvents which favor quaternization reactions, such as water, dimethyl formamide, methyl cyanide, lower alcohols, particularly lower alkanols such as methanol, etc.

The reaction temperature can vary between 10° and 150° C., and preferably between 20° and 100° C.

The reaction time depends upon the nature of the solvent, the initial reactants and the degree of polymerization desired.

In general, the initial reactants are reacted in equimolecular quantities, although it is possible to use either the diamine or dihalide in slight excess, said excess being less than 20 mole percent.

The resulting polycondensate is isolated at the conclusion of the reaction, if desired, either by filtration or by concentrating the reaction mixture.

It is possible to control the average length of the chains by adding, at the beginning or during the course of the reaction, a slight quantity (from 1 to 15 mole percent, with respect to one of the reagents) of a monofunctional reagent such as a tertiary amine or a monohalide. In this instance, at least a portion of the terminal groups of the resulting Formula I polymer is made up of either the tertiary amine group which is used or of the hydrocarbon group of the monohalide.

In general, the polymers of the present invention are soluble in at least one of the three solvents consisting of water, ethyl alcohol or a mixture of water and ethyl alcohol.

On evaporation of their solution, it is possible to obtain films which, in particular, have a good affinity for hair.

The polymers of the present invention can be used in cosmetic composition useful in the treatment of the hair and the skin. In particular, they improve the qualities of the hair, facilitate combing and protect the hair against damage due to the environment or to cosmetic treatments having a harmful effect.

The polymers of the present invention can also be used as agents to assist in the treatment of natural or synthetic textile fibers, such as antibacterial agents, dispersing agents or emulsifying or flocculating agents. For example, the polymers of the present invention can be used as preserving agents in adhesives or as additives in products for treating leather or cellulose derivatives, in particular, paper.

The following non-limiting examples illustrate the present invention.

EXAMPLE 1

Formula I polymer wherein:
$R_1 = R_2 = R_3 = R_4 = CH_3$,
$X^\ominus = Cl^\ominus$,
$A_1 = A_2 = -(CH_2)_3-$,
$A_3 = A_4 = (CH_2)_2$,
$p = 1$,
$X_1 = -NHCONH-$
and
$X_2$ represents $-CO-NH-C(CH_3)_2-(CH_2)_5-C(CH_3)_2-NH-CO-$.

There are heated to reflux in 50 cm³ of methanol, 0.1 mole of a diamine of the formula, $$\begin{array}{cc} CH_3 & CH_3 \\ | & | \\ N-(CH_2)_3-NH-CO-NH-(CH_2)_3-N \\ | & | \\ CH_3 & CH_3 \end{array}$$

and 0.1 mole of a dichloride of the formula, $$\begin{array}{cc} CH_3 & CH_3 \\ | & | \\ Cl(CH_2)_2CONH-C-(CH_2)_5-C-NHCO-(CH_2)_2Cl. \\ | & | \\ CH_3 & CH_3 \end{array}$$

After evaporation of the solvent, the residue is washed in ether and dried. The resulting polymer has a $Cl^\ominus$ content equal to 94% of the theoretical value.

The polymers of the following examples were prepared in a similar manner.

EXAMPLE 2

Formula I polymer wherein:
$R_1$, $R_2$, $R_3$, $R_4$, $A_1$, $X_1$, $A_2$, p and X are defined as in Example 1,
$A_3 = A_4 = CH_2$,
and
$X_2$ represents $-CO-NH-C(C_4H_9)_2-(CH_2)_{10}-C(C_4H_9)_2-NH-CO-$.

Ionic halogen content: 94.5% of theoretical value.

EXAMPLE 3

Formula I polymer wherein:
$R_1$, $R_2$, $R_3$, $R_4$, $X_1$, p and X are defined as in Example 1,
$A_1 = A_2 = (CH_2)_2$,
$A_3 = A_4 = CH_2$,
and
$X_2$ represents $-CO-NH-C(CH_3)_2-(CH_2)_6-C(CH_3)_2-NH-CO-$.

$Cl^\ominus$ content: 93% of theoretical value.

EXAMPLE 4

Formula I polymer wherein:
$R_1$, $R_2$, $R_3$, $R_4$, $A_1$, $A_2$, $X_1$ p and X are defined as in Example 1,
$A_3 = A_4 = CH_2$,
and
$X_2$ represents $-CO-NH-C(CH_3)_2-(CH_2)_{10}-C(CH_3)_2-NH-CO-$.

$Cl^\ominus$ content: 96.5% of theoretical value.

EXAMPLE 5

Formula I polymer wherein:
$R_1$, $R_2$, $R_3$, $R_4$, p and $X_1$ are defined as in Example 1,
$A_1 = A_2 = (CH_2)_2$,
$A_3 = A_4 = CH_2$,
$X^\ominus$ represents $Cl^\ominus$
and
$X_2$ represents $-CO-NH-C(C_2H_5)_2-(CH_2)_5-C(C_2H_5)_2-NH-CO-$.
$Cl^\ominus$ content: 92.1% of theoretical value.

EXAMPLE 6

Formula I polymer wherein:
$R_1$, $R_2$, $R_3$, $R_4$, p, $A_1$, $A_2$, $A_3$ and $A_4$ are defined as in Example 5,
$X_1$ represents $-O-CO-NH-(CH_2)_6-NH-CO-O-$,
$X^\ominus = Cl^\ominus$
and
$X_2$ represents $-CO-NH-C(C_4H_9)_2-(CH_2)_4-C(C_4H_9)_2-NH-CO-$.
$Cl^\ominus$ content: 94% of theoretical value.

EXAMPLE 7

Formula I polymer wherein:
$R_1$, $R_2$, $R_3$, $R_4$, $A_1$, $A_2$, p, $X_1$, $A_3$, $A_4$ and X are defined as in Example 1,
and
$X_2$ represents $-NH-CO-(CH_2)_4-CO-NH-$.
$Cl^\ominus$ content: 94.3% of theoretical value.

EXAMPLE 8

Formula I polymer wherein:
$R_1$, $R_2$, $R_3$, $R_4$, $A_1$, p, $X_1$, $A_2$ and X are defined as in Example 6,
$A_3 = A_4 = (CH_2)_2$,
and
$X_2$ represents $-NH-CO-C_6H_4-C_6H_4-CO-NH-$ (ortho).
$Cl^\ominus$ content: 94.2% of theoretical value.

EXAMPLE 9

Formula I polymer wherein:
$R_1$, $R_2$, $R_3$, $R_4$, p and X are defined as in Example 7,
$X_1 = -NH-CO(CH_2)_4-CONH-$,
$X_2 = -NH-CO-NH-$,
$A_3 = A_4 = (CH_2)_2$
and
$A_1 = A_2 = -CH_2-C(CH_3)_2-CH_2-$.
$Cl^\ominus$ content: 99% of theoretical value.

EXAMPLE 10

Formula I polymer wherein:
$R_1 = R_2 = R_3 = R_4 = C_8H_{17}$,
$A_1 = A_2 = CH_2$,
p = 1,
$A_3 = A_4 = (CH_2)_2$,
$X^\ominus = Cl^\ominus$,
$X_1$ represents

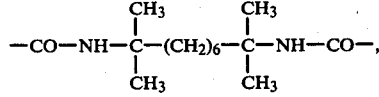

and $X_2$ represents $-NH-CO-C_6H_4-C_6H_4-CO-NH-$ (ortho).
$Cl^\ominus$ content: 90% of theoretical value.

EXAMPLE 11

Formula I polymer wherein:
$R_1 = R_2 = R_3 = R_4 = CH_3$,
$A_1 = A_2 = (CH_2)_2$,
p = 1,
$X_1 = -S-S-$,
$A_3 = A_4 = (CH_2)_4$,
$X^\ominus = Cl^\ominus$
and
$X_2$ represents $-O-CO-C_6H_4-CO-O-$ (para).
$Cl^\ominus$ content: 99% of theoretical value.

EXAMPLE 12

Formula I polymer wherein:
$R_1 = R_2 = R_3 = R_4 = C_2H_5$,
p = 1,
$X^\ominus = Cl^\ominus$,
$A_1 = A_2 = A_3 = A_4 = (CH_2)_3$,
$X_1$ represents $-NH-CO-CO-NH-$
and
$X_2$ represents $-O-CO-(CH_2)_6-CO-O-$.
$Cl^\ominus$ content: 84% of theoretical value.

EXAMPLE 13

Formula I polymer wherein:
$R_1 = R_2 = R_3 = R_4 = CH_3$,
p = 1
$A_1 = A_2 = -(CH_2)_2-C(CH_3)_2-$,
$A_3 = CH_2$,
$A_4 = (CH_2)_3$,
$X^\ominus = Cl^\ominus$,
$X_1$ represents $-NH-CO-C_6H_4-CO-NH-$ (para),
and
$X_2$ represents $-CO-O-$.
$Cl^\ominus$ content: 80% of theoretical value.

EXAMPLE 14

Formula I polymer wherein:
$R_1 = R_2 = R_3 = R_4 = CH_3$,
p = 1,
$X^\ominus = Cl^\ominus$,
$A_1 = A_2 = -CH_2-C(CH_3)_2-CH_2-$,
$A_3 = CH_2$,
$A_4 = (CH_2)_2$,
$X_1$ represents $-O-CO-(CH_2)_4-CO-O-$,
and
$X_2$ represents $-CO-NH-$.
$Cl^\ominus$ content: 82% of theoretical value.

EXAMPLE 15

Formula I polymer wherein:
$R_1 = R_2 = C_2H_5$,
$R_3 = R_4 = CH_3$,
$A_1 = A_3 = A_4 = CH_2$,
$A_2 = (CH_2)_3$,
p = 1,
$X^\ominus = Cl^\ominus$,
$X_1$ represents $-CO-NH-$
and
$X_2$ represents $-CO-O-(CH_2)_4-O-CO-$.
$Cl^\ominus$ content: 84% of theoretical value.

EXAMPLE 16

Formula I polymer wherein:
$R_1 = R_2 = C_2H_5$, $R_3 = R_4 = CH_3$,
$A_1 = A_3 = A_4 = CH_2$,
$A_2 = (CH_2)_3$,
$p = 1$,
$X^\ominus = Cl^\ominus$,
$X_1 = -CO-O-$
and
$X_2$ represents $-CO-O-(CH_2)_4-O-CO-$.
$Cl^\ominus$ content: 81% of theoretical value.

EXAMPLE 17

Formula I polymer wherein:
$R_1 = R_2 = R_3 = R_4 = C_4H_9$,
$A_1 = A_2 = CH_2$,
$A_3 = A_4 = (CH_2)_2$,
$p = 1$,
$X^\ominus = Cl^\ominus$, $X_1$ represents $-CO-O-(CH_2)_4-O-CO-$
and
$X_2$ represents $-NH-CO-(CH_2)_4-CO-NH-$.
$Cl^\ominus$ content: 86% of theoretical value.

I claim:

1. Polycationic polymer containing units of the formula

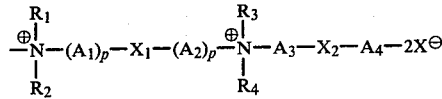

wherein $R_1$, $R_2$, $R_3$ and $R_4$, each independently represents a hydrocarbon group containing up to 20 carbon atoms, or at least one pair selected from the group consisting of $R_1$, $R_2$ and $R_3,R_4$, together with the nitrogen atom to which it is attached, forms a heterocycle selected from the group consisting of a heterocycle wherein the heteroatom is nitrogen or a heterocycle containing a nitrogen as a first heteroatom and a second heteroatom selected from the group consisting of oxygen and sulfur;

$A_1$, $A_2$, $A_3$ and $A_4$, each independently represents alkylene or arylene containing up to 20 carbon atoms;

p is 0 or 1;

when p is 0, $X_1$ represents $-C_6H_4-CO-C_6H_4-$, $-C_6H_4-CHOH-C_6H_4-$,

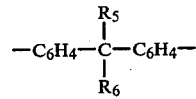

or $-C_6H_{10}-(CH_2)_n C_6H_{10}-$, wherein n is a whole number ranging from 1 to 6, $R_5$ and $R_6$ each independently represents hydrogen or alkyl, having up to 20 carbon atoms, or $R_5$ and $R_6$, together with the carbon atom to which they are attached, form a ring having 5 or 6 carbon atoms therein;

when p is 1, $X_1$ represents
$-N(R_7)-(CO-X_3)_y-CO-N(R_8)-$, $-CO-O-$, $-CO-NH-$, $-O-CO-NH-$, $-CO-X_4-CO-$, $-O-CO-X_5-CO-O-$, $-O-$, $-S-$, $-SO-$, $-SO_2-$, $-S-S-$ or $-N(R_9)-$, wherein $X_3$ represents alkylene, alkylene interrupted by an $-S-S-$ group, alkenylene, arylene, diaminoalkylene, diaminoarylene, dioxyalkylene, polyoxyalkylene, or dioxyarylene, or $X_3$ represents a direct covalent bond, $X_4$ represents diaminoalkylene, dioxyalkylene, diaminoarylene, dioxyarylene, polyoxyalkylene or dithioalkylene, $X_5$ represents alkylene, arylene, diaminoalkylene, diaminocycloalkylene or diaminoarylene, y is 0 or 1, $R_7$, $R_8$ and $R_9$ each independently represents hydrogen or alkyl containing up to 12 carbon atoms;

$X_2$ represents $-N(R_{10})-(CO-X_3)_z-CO-N(R_{11})-$, $-CO-O-$, $-CO-NH-$, $-O-CO-NH-$, $-CO-X_4-CO-$ or $-O-CO-X_5-CO-O-$, wherein $X_3$, $X_4$ and $X_5$ are defined above, z is 0 or 1 and $R_{10}$ and $R_{11}$ each independently represents hydrogen or alkyl containing up to 12 carbon atoms;

with the proviso that when p is 1 and $X_1$ represents a heteroatom selected from the group consisting of oxygen and sulfur, z is other than 0.

2. The polymer of claim 1 wherein $R_1$, $R_2$, $R_3$ and $R_4$ represent alkyl, cycloalkyl, alkenyl, aryl or aralkyl.

3. The polymer of claim 1 wherein when at least one of said pairs $R_1$, $R_2$ and $R_3$, $R_4$ together with the nitrogen atom to which it is attached, represents a ring, said ring has 5 or 6 carbon atoms therein.

4. The polymer of claim 1 wherein $R_1$, $R_2$, $R_3$ and $R_4$ represent alkyl having from 1 to 10 carbon atoms.

5. The polymer of claim 1 wherein $X_1$ represents $-NHCONH-$, $-S-S-$, $-O-CO-NH-$alkylene$-NH-CO-O-$, $-CO-NH-$alkylene$-NH-CO-$, $-NHCOCONH-$, $-NH-CO-C_6H_4-CO-NH-$, $-O-CO-$alkylene$-CO-O-$, $-CO-NH-$, $-CO-O-$ or $-CO-O-$alkylene$-O-CO-$.

6. The polymer of claim 1 wherein $X_2$ represents $-CO-NH-$alkylene$-NH-CO-$, $-NH-CO-$alkylene$-CO-NH-$, $-NH-CO-C_6H_4-C_6H_4-CO-NH-$, $-O-CO-C_6H_4-CO-O-$, $-O-CO-$alkylene$-CO-O-$, $-CO-O-$, $-CO-NH-$ or $CO-O-$(polyalkoxy)$-CO-$,
wherein aid alkylene moiety is defined as for $A_1$, $A_2$, $A_3$ and $A_4$ in claim 1.

7. The polymer of claim 1 wherein $X^\ominus$ represents an anion derived from a mineral acid or derived from a low molecular weight organic acid.

8. The polymer of claim 7 wherein $X^\ominus$ represents a halide, a sulfate, an acetate or a paratoluene sulfonate anion.

9. A process for preparing the polymer of claim 1 comprising polycondensing at least one amine having the formula

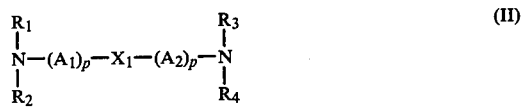 (II)

or

 (III)

with one or more dihalides having the formula

X—A₃—X₂—A₄—X or

X—(A₁)$_p$—X₁—(A₂)$_p$—X wherein R₁, R₂, A₁, p, X₁, A₂, R₃, R₄, A₃, X₂, A₄ and X have the meanings given in claim 1.

10. Polycationic polymer containing units of the formula

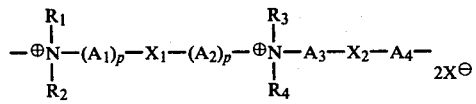

wherein R₁, R₂, R₃ and R₄ each independently represents alkyl containing up to 20 carbon atoms;

A₁, A₂, A₃ and A₄ each independently represents alkylene containing up to 20 carbon atoms;

p is 1;

X₁ represents —N(R₇)—(CO—X₃)$_y$—CO—N(R₈)—, —CO—O—, —CO—NH—, —O—CO—NH—, —CO—X₄—CO—, —O—CO—X₅—CO—O—, —O—, —S—, —SO—, —SO₂—, —S—S— or —N(R₉)— wherein X₃ represents alkylene, alkylene interrupted by an —S—S— group, alkenylene, arylene, diaminoalkylene, diaminoarylene, dioxyalkylene, polyoxyalkylene or dioxyarylene, or X₃ represents a direct covalent bond, X₄ represents diaminoalkylene, dioxyalkylene, diaminoarylene, dioxyarylene, polyoxyalkylene or dithioalkylene, X₅ represents alkylene, arylene, diaminoalkylene, diaminocycloalkylene or diaminoarylene, y is 0 or 1, R₇, R₈ and R₉ each independently represents hydrogen or alkyl containing up to 12 carbon atoms, X₂ represents —N(R₁₀)—(CO—X₃)$_z$—CO—N(R₁₁)—, —CO—O—, —CO—NH—, —O—CO—NH—, —CO—X₄—CO— or —OCO—X₅—CO—O—, wherein X₃, X₄ and X₅ are defined above, z is 0 or 1 and R₁₀ and R₁₁ each independently represents hydrogen or alkyl containing up to 12 carbon atoms, with the proviso that when X₁ represents a heteroatom selected from the group consisting of oxygen and sulfur, z is other than 0.

11. The polycationic polymer of claim 10 wherein X₁ represents —N(R₇)—(CO—X₃)$_y$—CO—N(R₈)—.

12. The polycationic polymer of claim 10 wherein X₁ represents —CONH—.

13. The polycationic polymer of claim 10 wherein X₁ represents —OCONH—.

14. The polycationic polymer of claim 10 wherein X₁ represents —CO—X₄—CO—.

15. The polycationic polymer of claim 10 wherein X₁ represents —OCOX₅—CO—O—.

16. The polycationic polymer of claim 10 wherein X₄ represents diaminoalkylene.

17. The polycationic polymer of claim 10 wherein X₄ represents diaminoarylene.

18. The polycationic polymer of claim 10 wherein X₅ represents diaminoalkylene.

19. The polycationic polymer of claim 10 wherein X₅ represents diaminocycloalkylene.

20. The polycationic polymer of claim 10 wherein X₅ represents diaminoarylene.

21. The polycationic polymer of claim 10 wherein X₂ represents —N(R₁₀)—(CO—X₃)—CO—N(R₁₁)—.

22. The polycationic polymer of claim 10 wherein X₂ represents —CONH—.

23. The polycationic polymer of claim 10 wherein X₂ represents —OCONH—.

24. The polycationic polymer of claim 10 wherein X₂ represents —COX₄CO—.

25. The polycationic polymer of claim 10 wherein X₂ represents —OCOX₅CO—O—.

26. Polycationic polymer containing units of the formula

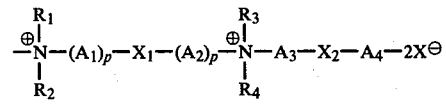

wherein R₁, R₂, R₃ and R₄ each independently represents CH₃, C₈H₁₇, C₂H₅ or C₄H₉, A₁, A₂, A₃ and A₄ each independently represents (CH₂)₃, (CH₂)₂, —CH₂—C(CH₃)₂—CH₂—, CH₂, —(CH₂)₂—C(CH₃)₂—, or —(CH₂)₄, p is 1, X₁ represents —NHCONH—, —O—CO—NH—(CH₂)₆—NH—CO—O—, —NH—CO—(CH₂)₄—CONH—,

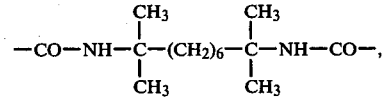

—S—S—, —NH—CO—CO—NH—, —NH—CO—C₆H₄—CO—NH—, —O—CO—(CH₂)₄—CO—O—, —CONH—, —CO—O— or —CO—O—(CH₂)₄—O—CO—,

X₂ represents —CO—NH—C(CH₃)₂—(CH₂)₅—C(CH₃)₂—NH—CO—, —CO—NH—C(C₄H₉)₂—(CH₂)₁₀—C(C₄H₉)₂—NH—CO—, —CO—NH—C(CH₃)₂—(CH₂)₆—C(CH₃)₂—NH—CO—, —CO—NH—C(CH₃)₂—(CH₂)₁₀—C(CH₃)₂—NH—CO—, —CO—NH—C(C₂H₅)₂—(CH₂)₅—C(C₂H₅)₂—NH—CO—, —CO—NH—C(C₄H₉)₂—(CH₂)₄—C(C₄H₉)₂—NH—CO—, —NH—CO—(CH₂)₄—CO—NH—, —NH—CO—C₆H₄—C₆H₄—CO—NH—, —NH—CO—NH—, —O—CO—C₆H₄—CO—O—, —O—CO—(CH₂)₆—CO—O—, —CO—O—, —CONH— or —CO—O—(CH₂)₄—O—CO—, and X$^\ominus$ is Cl$^\ominus$.

27. Polycationic polymer containing units of the formula

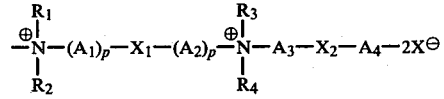

wherein each of R₁, R₂, R₃ and R₄ is CH₃, X$^\ominus$ is Cl$^\ominus$, each of A₁ and A₂ is —(CH₂)₃—, each of A₃ and A₄ is (CH₂)₂, p is 1, X₁ is —NHCONH— and X₂ is —CO—NH—C(CH₃)₂—(CH₂)₅—C(CH₃)₂—NH—CO—.

* * * * *